United States Patent [19]

Hofer

[11] Patent Number: 4,820,709

[45] Date of Patent: * Apr. 11, 1989

[54] 6-THIOXANTHINE DERIVATIVES

[75] Inventor: Peter Hofer, Liestal, Switzerland

[73] Assignee: Euroceltique, S.A., Luxembourg, Luxembourg

[*] Notice: The portion of the term of this patent subsequent to Dec. 1, 2004 has been disclaimed.

[21] Appl. No.: 75,937

[22] Filed: Jul. 22, 1987

Related U.S. Application Data

[63] Continuation of Ser. No. 699,254, Feb. 7, 1985, Pat. No. 4,710,503.

[51] Int. Cl.$^4$ .................. C07D 473/06; A61K 31/52
[52] U.S. Cl. ...................................... 514/263; 544/267
[58] Field of Search ............... 514/263; 544/267, 266, 544/276, 277

[56] References Cited

U.S. PATENT DOCUMENTS 4,546,182 10/1985 Kjellin et al. ...................... 544/267
4,710,503 12/1987 Hofer ................................. 514/263

OTHER PUBLICATIONS

Armitrage et al., British Journal Pharmacology (1961), pp. 196–207.

Primary Examiner—Nicholas S. Rizzo
Attorney, Agent, or Firm—Steinberg & Raskin

[57] ABSTRACT

Compounds of the formula

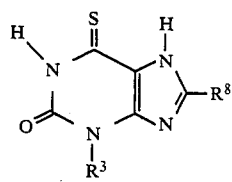

wherein
$R^3$ is ethyl, n-propyl or n-butyl, and
$R^8$ is hydrogen, methyl or ethyl,
exhibit bronchodilating activity with reduced side effects and increased half-like. A method of achieving bronchodilation with reduced undesired effects (diuresis, CNS activity), by administering the said compounds to a patient, is also provided.

13 Claims, No Drawings

6-THIOXANTHINE DERIVATIVES

This is a continuation of application Ser. No. 699,254, filed 2/7/85, now U.S. Pat. No. 4,710,503.

BACKGROUND OF THE INVENTION

Certain xanthine derivatives have been previously used for providing antiasthmatic bronchodilating therapeutic activity. For example, Enprofylline (3-propylxanthine) and theophylline (1,3-dimethylxanthine) are both known antiasthmatics and bronchodilators. Allergy 1983, 38, 75–79 analyzes the bronchospasmolytic activity of Enprofylline, while Medical Hypotheses 8 (1962): 515–526 observes that Enprofylline is four to five times more potent than theophylline, and does not exhibit the adenosine antagonistic activity of theophylline.

However, Enprofylline possesses a disadvantageously short half-life of less than two hours, and also retains an extremely undesirable emetic effect, as is the case with theophylline.

Only one particular 1-unsubstituted thioxanthine derivative, notably 3-isobutyl-6-thioxanthine, has been prepared and examined for bronchodilating activity (Brit. J. Pharmacol. (1961), 17, 196–207). This compound (Compound No. 30 in Table 4) was tested along with 6-thiotheobromines (3,7-disubstituted 6-thioxanthines) and 6-thiocaffeines (1,3,7-trisubstituted 6-thioxanthines). Only two experiments examining the bronchodilating activity of this compound were carried out, and it was noted that the number of experiments carried out was small and the data had not been subjected to any statistical examination.

It has now been surprisingly found that certain 6-thioxanthine derivatives not only result in improved bronchodilating activity, but also result in reduced side effects while having improved half-life over previously-used corresponding xanthine derivative bronchodilators.

SUMMARY OF THE INVENTION

The present invention is directed to certain novel xanthine derivatives which provide improved bronchodilating activity with reduced side effects. The compounds also have the advantage of increased half-life as compared to known bronchodilators.

Accordingly, it is an object of the present invention to provide improved bronchodilation in individuals suffering from asthma or asthmatic symptoms.

It is also an object of the present invention to provide improved bronchodilation and reduced undesired effects.

It is another object of the present invention to provide new compounds, compositions and methods for achieving improved bronchodilating activity such compounds and compositions having improved stability over time.

These and other objects are attained by the present invention, which is directed to a compound of the formula

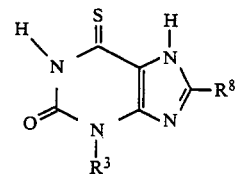

wherein
$R^3$ is ethyl, n-propyl or n-butyl, and
$R^8$ is hydrogen, methyl, or ethyl,
such a compound exhibiting improved bronchodilating activity with reduced undesired effects, along with having an increased stability, notably increased half-life over previously-used corresponding compounds and compositions. The present invention also provides for a method of achieving bronchodilation with reduced side effects, by administering to a patient requiring the same, a bronchodilating effective amount of a compound of the above formula.

The compounds of the present invention have increased invivo stability, i.e., increased half-life, over other corresponding xanthine derivatives that have been used for bronchodilation, notably Enprofylline. Additionally, the present invention provides for improved bronchodilating activity with reduced undesired effects as compared with other xanthine derivatives, such as Enprofylline.

DETAILED DESCRIPTION OF THE PREFERRED EMBODIMENTS

The 3-ethyl-, 3-propyl-, and 3-n-butyl-6-thioxanthines of the present invention, may be optionally substituted with methyl or ethyl at the 8 position as is clear in the above structural formula. Especially preferred compounds are 3-ethyl-6-thioxanthine and 3-propyl-6-thioxanthine. The compounds of the invention may be synthesized from appropriate precursors according to the procedure of Wooldridge and Slack, at J. Chem. Soc. 1962, 1863–1868.

The compounds of the present invention may be incorporated into a pharmaceutical composition for administration to an individual, together with any conventional pharmaceutically acceptable carriers or excipients. The compounds may be incorporated into such a composition in the free form thereof, or in the form of a non-toxic, pharmaceutically acceptable salt. Pharmaceutically acceptable salts of the compounds of the present invention may be prepared by conventional reaction with equivalent amounts of organic or inorganic bases. Such pharmaceutically acceptable salts include, but are not limited to, potassium, sodium, choline, and basic amino acid salts.

The compositions of the present invention may be administered parenterally in combination with conventional injectable liquid carriers, such as water or suitable alcohols. Conventional pharmaceutical adjuvants for injection such as stabilizing agents, solubilizing agents, and buffers, may be included in such injectable compositions. These compositions may be injected intramuscularly, intraperitoneally, or intravenously.

Compositions according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, capsules, lozenges, aqueous or oily suspensions, emulsions, or dry powdered form suitable for reconstitution with water or other suitable liquid medium before use, for immediate or controlled release.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically as an aerosol. In a particular aspect of the present invention, bronchodilation is achieved with reduced emesis, by administering to a patient requiring the same, a bronchodilating effective amount of a compound of the above-noted formula.

The dosage generally utilized for the purposes of the invention vary within wide limits and will depend on various factors such as the individual patient. A suitable oral dosage may be 50–1000 mg given 1–4 times a day, while a suitable parenteral dose may be 20–500 mg.

The present invention will be explained in further detail, by way of the following examples:

EXAMPLE I

3-ethyl-6-thioxanthine

A suspension of 11.7 g. (65 mM.) of 3-ethylxanthine in 110 ml. pyridine was treated with 23.5 g. (106 mM.) of phosphorus pentasulfide in 135 ml. of pyridine. The temperature rose from 25° C. to 40° C.

The reaction mixture was refluxed (with dissolution) for 4 hours and then cooled, with 350 ml. of water then being added slowly. The resulting bright green suspension was concentrated to about 200 ml., and the solid was then collected.

The still humid product was suspended in 100 ml. of 2N NaOH, with the filtrate then being collected and acidified with 5N HCl to a pH of 2–3.

The resulting precipitate was then collected and dissolved in 50 ml. of 2N NaOH, with the resulting solution being treated with 0.4 g. of charcoal, followed by filtering and acidification again with 2N HCl to a pH of 2.

The resulting precipitate was collected, washed with ice water, and dried. 10.3 g. (80.7% yield) of 3-ethyl-6-thioxanthine, having a melting point of 278°–280° C., was obtained.

Analysis Calculated For $C_7H_8N_4OS$ (m.w. 196.24): Calculated: C, 42.85%, H, 4.11%; N, 28.55%; O, 8.15%; S, 16.34%. Found: C, 42.97%; H, 4.14%; N, 28.44%; O, 7.96%; S, 16.49%.

EXAMPLE II

3-propyl-6-thioxanthine

A suspension of 9.32 g. (48 mM) of 3-propylxanthine in 80 ml. of pyridine, was treated with 17.33 g. (78 mM.) of phosphorus pentasulfide in 80 ml. of pyridine, and worked up analogously to Example I. 8.9 g. of 3-propyl-6-thioxanthine was obtained. Recyrstallization from methanol-acetone gave 7.4 g. (59% yield) of needles with a melting point of 249°–250° C.

Analysis Calculated For $C_8H_{10}N_4OS$ (m.w. 210.26): Calculated: C, 45.70%; H, 4.79%; N, 26.65%; O, 7.61%; S, 15.25%. Found: C, 45.88%; H, 4.84%; N, 26.66%; O, 7.36%; S, 15.26%.

EXAMPLE III

3-butyl-8-ethyl-6-thioxanthine 11.8 g (50 mM.) of 3-butyl-8-ethyl-xanthine (mp 304°–9° C., and 18.2 g (82 nM.) of phosphorus pentasulfide were refluxed in 170 ml of pyridine for 2 hrs. The solution was cooled to ambient temperature and treated slowly with 110 ml. of water (exothermic). The suspension was concentrated to 100 ml. in vacuo at 60° C., further diluted with 140 ml. of water, and concentrated again to about 120 ml. The crude product was collected and washed with ice water. The dried material (11.1 g.) was dissolved in about 100 ml. of chloroform, and the solution filtered through 55 g. of silicagel. The chloroform was evaporated and the residue crystallized from acetone-ether: 7.2 g. (57.5%) of 3-butyl-8-ethyl-6-thioxanthine, mp. 206°–7° C. From the mother liquor, a second crop of 2.1 g. (16.3%) was obtained.

Analysis calculated for $C_{11}H_{16}N_4OS$ (m.w. 252.3): calc.: C, 52.36%; H, 6.39%; N, 22.20%; S, 12.70%. found: C, 52.26%; H, 6.48%; N, 22.25%; S, 12.66%.

EXAMPLE IV 3-ethyl-8-methyl-6-thioxanthine, 3-ethyl-8-ethyl-6-thioxanthine, 3-propyl-8-methyl-6-thioxanthine, 3-propyl-8-ethyl-6-thioxanthine, 3-butyl-6-thioxanthine, and 3-butyl-8-methyl-6-thioxanthine may all be synthesized in a similar fashion to 3-ethyl-6-thioxanthine, 3-propyl-6-thioxanthine, or 3-butyl-8-ethyl-6-thioxanthine as outlined in Examples 1, 2 and 3.

The preceding description of the present invention is merely intended as exemplary, and is not intended to limit the scope thereof in any way.

What is claimed is:

1. A compound selected from the group consisting of 3-ethyl-8-methyl-6-thioxanthine, 3-ethyl-6-thioxanthine, 3-ethyl-8-ethyl-6-thioxanthine, 3-butyl-8-methyl-6-thioxanthine, and pharmaceutically acceptable salts thereof.

2. A compound of claim 1, which is 3-ethyl-8-methyl-6-thioxanthine.

3. The compound of claim 1 which is, 3-ethyl-8-ethyl-6-thioxanthine.

4. The compound of claim 1 which is, 3-butyl-8-methyl-6-thioxanthine.

5. The compound of claim 1 which is, 3-ethyl-6-thioxanthine.

6. Method of achieving bronchodilation with reduced side effects, which comprises administering to a patient requiring the same, a bronchodilation effective amount of a compound selected from the group consisting of 3-ethyl-8-methyl-6-thioxanthine, 3-ethyl-6-thioxanthine, 3-ethyl-8-ethyl-6-thioxanthine, 3-butyl-8-methyl-6-thioxanthine, and pharmaceutically acceptable salt thereof.

7. The method of claim 6, which comprises administering a bronchodilation effective amount of 3-ethyl-8-methyl-6-thioxanthine.

8. The method of claim 6, which comprises administering a bronchodilation effective amount of 3-ethyl-8-methyl-6-thioxanthine.

9. The method of claim 6, which comprising administering a bronchodilation effective amount of 3-butyl-8-methyl-6-thioxanthine.

10. The method of claim 6, which comprises administering a bronchodilation effective amount of 3-ethyl-6-thioxanthine.

11. Composition for effecting bronchodilation with reduced undesired effects, said composition comprising a bronchodilating effective amount of the compound of claim 1 distributed in a pharmaceutically acceptable carrier.

12. Composition according to claim 11 in a form for oral administration.

13. Composition according to claim 11 in a form for parenteral administration.